US008666102B2

(12) United States Patent
Bruckhoff et al.

(10) Patent No.: US 8,666,102 B2
(45) Date of Patent: Mar. 4, 2014

(54) HEARING SYSTEM COMPRISING AN EARPIECE (75) Inventors: Henning Bruckhoff, Garbsen (DE);
Wolfgang Huep, Hanover (DE);
Juergen Brinkmann, Lehrte (DE);
Peter Boschung, Schmitten (CH)

(73) Assignee: Phonak AG, Stafa (CH)

( * ) Notice: Subject to any disclaimer, the term of this patent is extended or adjusted under 35 U.S.C. 154(b) by 174 days.

(21) Appl. No.: 13/322,008

(22) PCT Filed: Jun. 12, 2009

(86) PCT No.: PCT/EP2009/057299
§ 371 (c)(1),
(2), (4) Date: Nov. 22, 2011

(87) PCT Pub. No.: WO2009/153221
PCT Pub. Date: Dec. 23, 2009

(65) Prior Publication Data
US 2012/0063622 A1 Mar. 15, 2012

(51) Int. Cl.
*H04R 25/00* (2006.01)
*H04R 1/10* (2006.01)
(52) U.S. Cl.
CPC .......... *H04R 1/1016* (2013.01); *H04R 2201/10* (2013.01)
USPC .......................................... 381/328; 381/380
(58) Field of Classification Search
USPC .................. 381/322, 328, 380, 312; 379/430; 455/575.2
See application file for complete search history.

(56) References Cited

U.S. PATENT DOCUMENTS

| 6,661,901 | B1 | 12/2003 | Svean et al. |
| 2005/0250559 | A1* | 11/2005 | Nassimi .................... 455/575.2 |
| 2006/0067556 | A1 | 3/2006 | Bailey et al. |

FOREIGN PATENT DOCUMENTS

| EP | 1 071 307 A1 | 1/2001 |
| EP | 1 355 508 A2 | 10/2003 |
| EP | 1 377 113 A2 | 1/2004 |
| EP | 1 448 014 A1 | 8/2004 |
| EP | 1 674 059 A1 | 6/2006 |
| EP | 1 364 553 B1 | 9/2006 |
| GB | 833 506 | 4/1960 |
| WO | 2007/014950 A2 | 2/2007 |
| WO | 2007/082579 A2 | 7/2007 |
| WO | 2007/147416 A1 | 12/2007 |
| WO | 2009/047369 A2 | 1/2009 |

* cited by examiner

*Primary Examiner* — Tuan D Nguyen
(74) *Attorney, Agent, or Firm* — Roberts Mlotkowski Safran & Cole, P.C.; David S. Safran (57) ABSTRACT A hearing system includes at least one earpiece having a shell, an elongate retention element attached to the shell, and an insert unit. The shell has a sound tube portion carrying a soft tip for insertion into the user's ear canal, an outwardly oriented interface portion for detachably receiving the insert unit, and an engagement portion between the sound tube portion and the interface portion for engaging with the tragus/antitragus region of the ear, wherein the material and the dimensions of the retention element are such that the retention element can engage the user's concha by manual deformation by the user, and wherein the insert unit is a filter unit with at least one sound attenuation filter, or is an active electronic unit with at least a loudspeaker, and with an external electronic unit, which is worn on the user's body below the user's neck.

43 Claims, 5 Drawing Sheets

HEARING SYSTEM COMPRISING AN EARPIECE

BACKGROUND OF THE INVENTION

1. Field of the Invention

The invention relates to a hearing system including an earpiece comprising a shell and an insert unit detachably connected to the shell.

2. Description of Related Art

A system of the type to which the invention relates may be used for wireless communication with other persons if the insert unit is an active electronic unit which is connected via a cable to an external electronic unit. Typically, the communication is bidirectional, with the active unit then comprising at least one microphone for capturing the user's voice. The external electronic unit typically comprises a mobile phone or a radio device. The external audio signals received by the external communication device are supplied to the loudspeaker of the active unit, and the audio signals captured by the microphone(s) of the active unit are transmitted to a corresponding wireless communication device used by another person. In addition to the communication function, the hearing system may provide for a hearing protection function, which requires an appropriate design of the earpiece which has to act as a hearing protection earplug. In this case, for enabling a noise level dependent dynamic hearing protection function, the active unit may be provided with a microphone for capturing ambient sound, and the external unit may be provided with an appropriate audio signal processing unit which supplies the processed ambient audio signals to the loudspeaker of the active unit. There are also cases in which the system comprises only the dynamic hearing protection function, but not a bidirectional communication function.

In the simplest case, for realizing a passive hearing protection function, the insert unit comprises at least one acoustic attenuation filter, but no electronic components. By selecting different filters, the attenuation may be individually adjusted to some extent.

The shell of the earpiece, in particular, if a hearing protection function is desired, may be manufactured as a customized shell having a shape which is adapted to the individual shape of the user's ear, usually by manufacturing the shell according to an impression taken from the user's ear. Customized shells provide for optimal retention within the user's ear and for optimized acoustic sealing. While customized earpieces may provide for improved retention and sealing properties compared to generic earpieces (i.e. earpieces having a standard shape), manufacturing of customized earpieces is more complicated, in particular because it involves participation of the user for taking an impression of the user's ear.

Examples of customized earpieces for hearing protection systems comprising bidirectional communication functions are found in European Patent Application EP 1 674 059 A1, International Patent Application Publication WO 2007/082579 A2 and U.S. Pat. No. 6,661,901 B1. An example for an active hearing protection system without bidirectional communication function is described in European Patent Application EP 1 071 307 A1. Further examples of earpiece communication systems are found in International Patent Application Publication WO 2009/047369 A2.

It is known, for example, from German Utility Model DE 297 18 483 U1, European Patent Application EP 1 448 014 B1, and International Patent Application Publications WO 2007/014950 A2 or WO 2007/147416 A1, to provide hearing aids to be worn at least partly in the ear canal with an elastic C-shaped bow-like element for improving retention of the shell in the ear canal, wherein the retention force is provided by the elastic deformation of the retention element which engages with the concha when worn by the user. U.S. Patent Application Publication US 2006/0067556 A1 relates to an earpiece comprising a bow-like retention element and a sound channel, which may be connected in a releasable manner with an acoustic device which may be a hearing aid or a wireless communication device. The wireless communication device may form a wireless headset for a mobile phone.

European Patent Application EP 1 364 553 B1 relates to an earpiece comprising an elastic concha bow and a sound channel as well as a microphone and a loudspeaker which are connected via a cord with an external audios signal processing unit for realizing a headset for wireless communication.

European Patent Application EP 1 377 113 A1 relates to a headset comprising an earpiece which carries a boom microphone and comprises an elastic concha bow.

SUMMARY OF THE INVENTION

It is an object of the invention to provide for a hearing system comprising an earpiece, wherein the earpiece is easy to be manufactured and nevertheless provides for good retention within the user's ear, wherein the earpiece is as compact as possible and wherein the system provides for high functional flexibility.

SUMMARY OF THE INVENTION

According to the invention, these objects are achieved by a hearing system of the initially mentioned type which is provided with a sound tube portion carrying a soft tip which is to be inserted into the user's ear canal, an outwardly oriented interface portion for detachably receiving the insert unit, and an engagement portion located between the sound tube portion and the interface portion for engaging with the tragus/anti-tragus region of the ear, wherein a material and dimensions of the retention element are such that the retention element can be brought into engagement with a user's concha by manual deformation by the user, and wherein the insert unit is a filter unit comprising at least one of a sound attenuation filter and an active electronic unit comprising at least a loudspeaker, with an external electronic unit, which is to be worn at a user's body below a user's neck, being connected to the active electronic unit via a cable connection. By cooperation of the elongate flexible retention element, the sound tube portion with the soft tip and the engagement portion, good retention within the user's ear is achieved. Due to the good retention provided by the earpiece, the need for a customized shell is eliminated. High flexibility of the system is achieved by the outwardly oriented interface portion which receives the insert unit in a detachable manner.

If the insert is an active electronic unit, the active unit can be kept as simple and as small as possible by connecting the active unit via a cable connection to an external electronic unit, since it needs to include only the loudspeaker, and if desired, the microphone(s). The insert unit may realize the function of passive hearing protection with adjustable attenuation levels with or without communication function, a level dependent (i.e., active) hearing protection with or without communication function, or a communication function without hearing protection (in the latter case the earpiece acts as a headset which may be worn only on one side). Preferably, not only the insert unit, but also the soft tip and the retention element are detachably connected to the earpiece.

These and further objects, features and advantages of the present invention will become apparent from the following description when taken in connection with the accompanying drawings which, for purposes of illustration only, show several embodiments in accordance with the present invention.

DETAILED DESCRIPTION OF THE INVENTION

Figure 1:
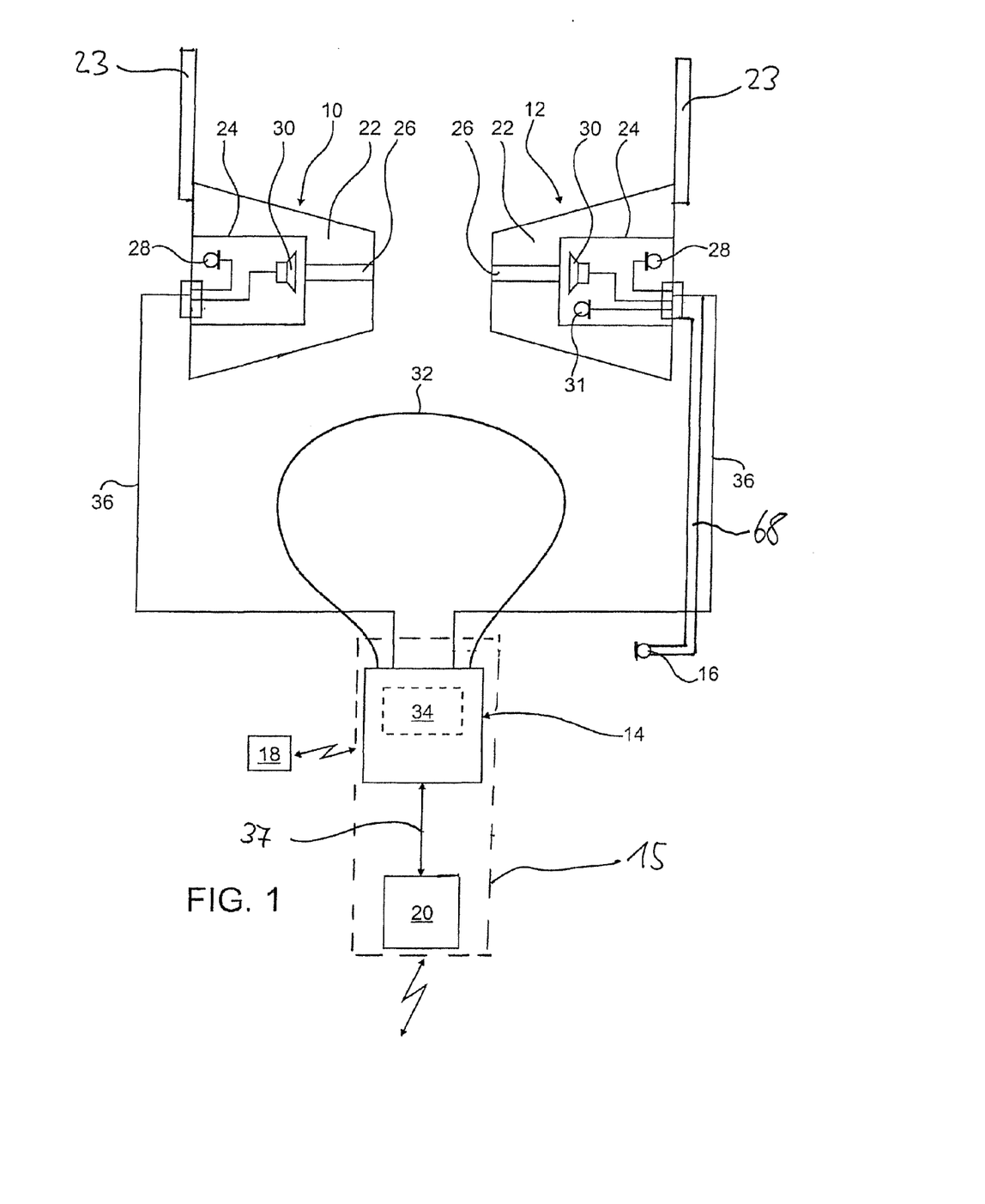
FIG. 1 is a block diagram of the most relevant electronic components of an embodiment of a system according to the invention.

The hearing system shown in FIG. 1 comprises a left ear earpiece 10, a right ear earpiece 12, an external electronic unit 15 and an active electronic unit 24 for each of the earpieces 10, 12. Each earpiece 10, 12 comprises a shell 22 which has a receptacle 42 into which the active unit 24 is inserted in a releasable manner. The shell 22 is provided with a sound channel 26 through which the active unit 24 is acoustically connected to the ear canal. The active unit 24 comprises a first microphone 28 for capturing audio signals from ambient sound and a loudspeaker 30 for providing audio signals into the user's ear canal via the sound channel 26. One of the active units 24 also may comprise a second microphone 31 for capturing the user's voice. Alternatively, one of the active units 24 may be provided with a boom microphone 16 carried by an elastic bow 68. An elongate elastic retention element 23 is fixed at the shell 22. It is noted that the representation of the earpieces 10, 12 in FIG. 1 is not representative of the actual geometry of the earpieces 10, 12 (which is shown in FIGS. 2 to 9)

The external unit 15 comprises a wireless communication device 20, such as a mobile phone or a radio device, and a central unit 14 which may be worn on the user's body, e.g., by a loop 32 around the user's neck. The central unit 14 comprises an audio signal processing unit 34 for receiving in processing audio signals captured by the microphones 28, 31 and for supplying the loudspeaker 30 with audio signals to be reproduced to the user's ear. To this end, the active unit 24 is connected to the central unit 14 via cable connections 36. The processed audio signals are supplied to the wireless communication device 20 via a cable connection 37 in order to be transmitted to a wireless communication device used by another person. In the other hand, audio signals received from such other wireless communication device by the device 20 are supplied via the cable connection 37 to the central unit 14 in order to be reproduced by the loudspeaker 30.

The boom microphone may be omitted if the central unit 14 is able to performing blind source separation (BSS) on the audio signals from the microphones 28, 31 in order to separate the user's voice from background noise. To this end, each microphone 28 has to be acoustically oriented towards ambient in order to capture primarily ambient sound, and the microphone 31 has to be acoustically oriented towards the ear canal in order to capture primarily the user's voice.

Preferably, the earpieces 10, 12 are designed to provide a hearing protection function, wherein a sound attenuation of at least 10 dB averaged over the audible frequency range should be provided. In this case, the microphones 28, the central unit 14 and the loudspeakers 30 may be used to provide an active hearing protection function, wherein, depending on the noise level, sound captured by the microphone 28 is supplied into the user's ear canal via the central unit 14, the loudspeaker 30 and the sound channel 26. For example, if the ambient noise level is low, ambient sound captured by the microphone 28 may be supplied by the loudspeaker 30 at a close to natural level in order to enable direct communication with a person speaking to the user of the hearing system despite wearing the hearing protection earpieces 10, 12.

While a combination of an active hearing protection function and a wireless communication function may be preferred, the system may be modified in such a manner that only the active hearing protection function is realized (in this case, the wireless communication device 20 and the microphones 31 and the boom microphone 16 would be omitted) or that only the wireless communication function may be realized (in this case, the earpieces 10, 12 need not to provide significant acoustic attenuation). When realizing a communication function without hearing protection, one of the two earpieces, 10 12 may be omitted.

The system of FIG. 1 may comprise a remote control 18 and/or a push-to-talk (PTT) button (not shown).

The system of FIG. 1 may realize a passive hearing protection function rather than an active hearing protection function. In this case, no ambient sound would be reproduced via the speaker 30. Rather, the active unit 24 then may include at least one (passive) acoustic attenuation filter (not shown) which may be exchangeable in order to adjust the acoustic attenuation provided by the earpiece 10, 12.

Figure 10:
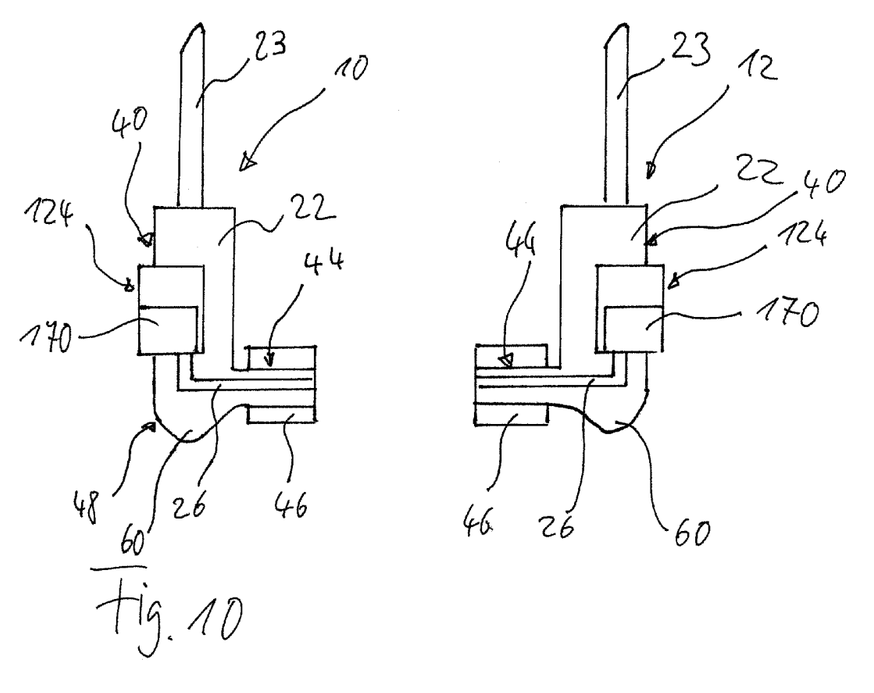
FIG. 10 is a schematic view of an earpiece of the invention which acts as a passive hearing protection device.

In FIG. 10 a passive hearing protection system is shown which does not include any electronic components. In this case the active unit 24 of FIG. 1 is replaced by an insert unit 124 comprising at least one passive acoustic attenuation filter 170 which preferably is exchangeable in order to individually adjust the attenuation provided by the earpiece 10, 12.

Examples of an earpiece 10, 12 according to the invention is shown in FIGS. 2 to 9.

The shell 22 has a standard shape, i.e., the shape is not specifically adapted to the individual shape of the user's ear, and comprises an outwardly oriented interface portion 40 comprising a receptacle 42 for detachably receiving the active unit 24, a sound tube portion 44 for carrying a soft tip 46 which is to be inserted into the user's ear canal, and an engagement portion 48 located between the sound tube portion 44 and the interface portion 40 for engaging with the tragus/antitragus region of the user's ear. Preferably the shell 22 is made of a thermoplastic.

The retention element 23 is connected to the engagement portion 48 in a releasable manner. The retention element 23 preferably is provided in two different sizes, wherein the user may select the most appropriate one of the two sizes. The retention element 23 may be changed or removed for cleaning purposes at any time; typically it has a lifetime of several months. Preferably, the retention element 23 is made of a material having a hardness of 60 Shore A to 90 Shore A. According to the example shown in the figures, the retention element 23 is substantially straight and has a constant cross section with a tapered end. It extends substantially perpendicular with regard to the axial direction of the sound tube portion 44 and substantially tangential with regard to the interface portion 40 and is located below the upper end 50 of the interface portion 40 (see in particular FIG. 5). In general, the material and the dimensions of the retention element 23 are selected such that the retention element 23 can be brought into engagement with the user's concha and helix area by manual deformation by the user, wherein the retention element 23 is bent according to the shape of the user's ear (see FIG. 7).

Figure 2:
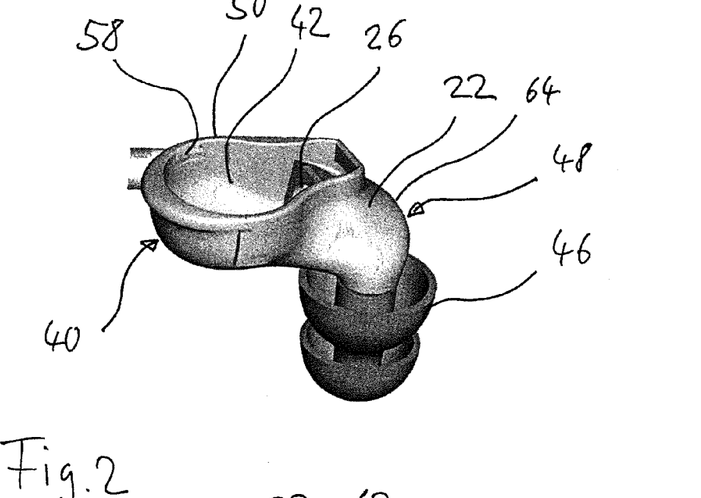
FIG. 2 is a perspective view of an example of an earpiece according to the invention.
Figure 3:
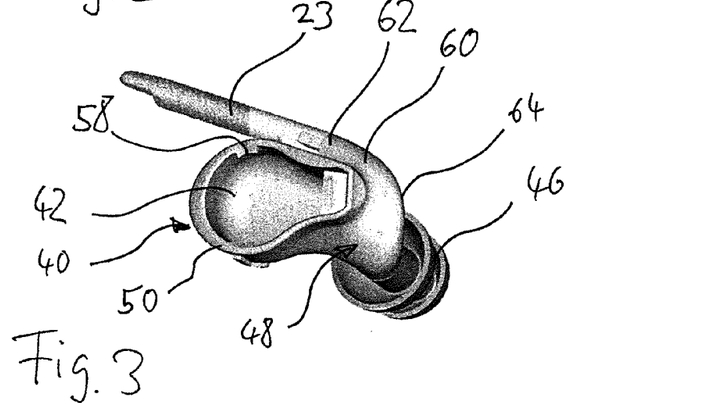
FIG. 3 is a view like FIG. 1, however seen at a different angle.

The soft tip 46 may be made of foam (see FIG. 8) or of silicone (see FIG. 2). The soft tip 46 is exchangeable so that it can be changed at any time (typically, the foam tip has a lifetime of some days or weeks, whereas the silicone tip has a lifetime of several months); the silicone tip may be removed for cleaning purposes. The soft tip 46 preferably is provided in three different sizes, wherein the user may select the most appropriate size in order to achieve a high fit rate. The soft tip 46 allows the earpiece 10, 12 to be positioned in such a manner in the concha that it does not extend out of the pinna.

Figure 4A:
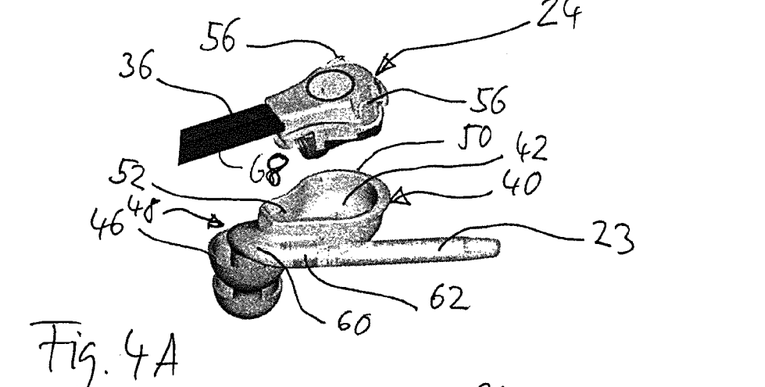
FIGS. 4A and 4B are perspective views of the earpiece of FIGS. 1 to 4 seen at a still different angle, wherein the earpiece is shown prior to and after connecting at to an active unit, respectively.
Figure 4B:
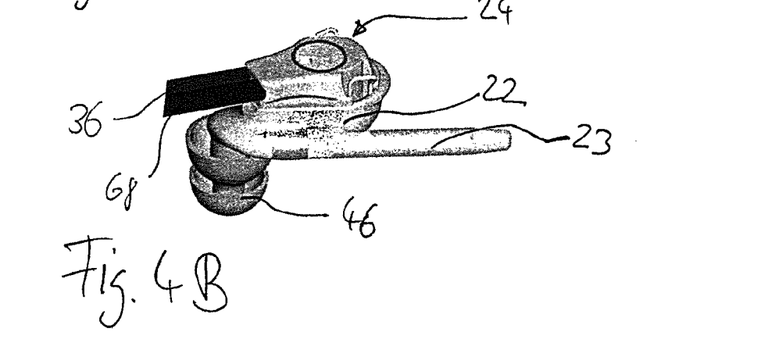

The sound tube portion 44 preferably has a length of 4 to 7 mm and is substantially straight. As shown in FIG. 4, it may be provided with beads 66 for promote retention of the soft tip 46 on the sound tube portion 44. For achieving enhanced wearing comfort, the sound tube portion 44 may be bendable, i.e. flexible with regard to bending forces, i.e., forces acting in a direction perpendicular to the axial direction of the sound tube portion 44, but it is substantially rigid along its axial direction. The sound tube portion 44 also may be twistable around its longitudinal axis to some extent.

Figure 6:
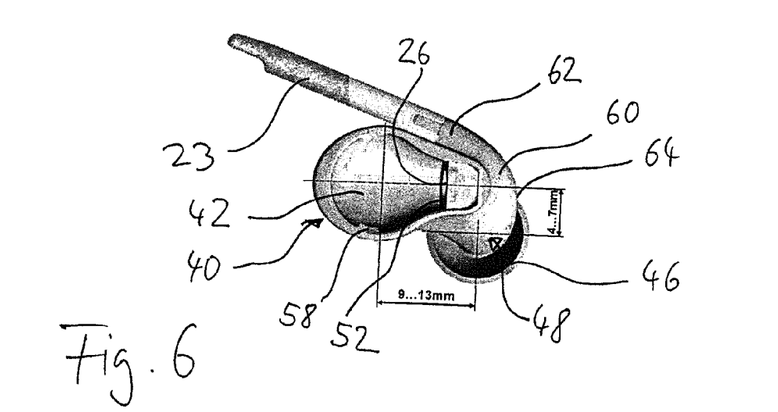
FIG. 6 is a top view of the earpiece of FIGS. 2 and 3.
Figure 7:
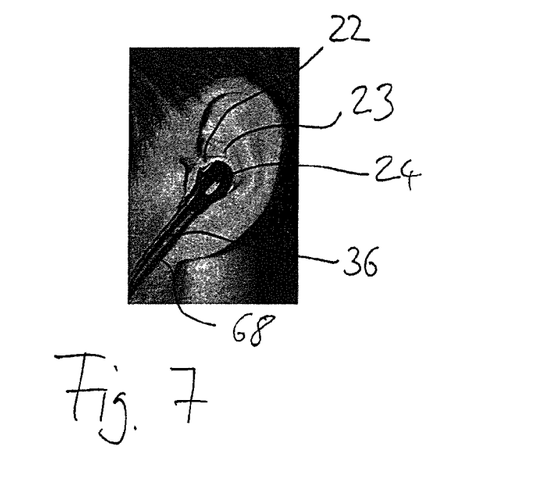
FIG. 7 is a view of the earpiece of FIG. 4B when worn by a user.
Figure 8:
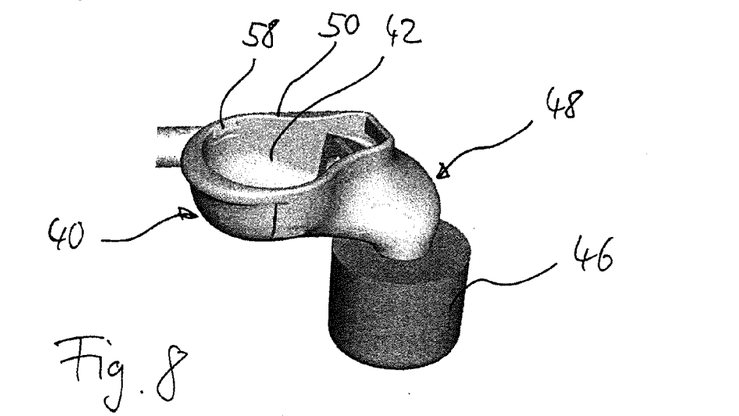
FIG. 8 is a view like FIG. 2, wherein the earpiece is provided with a different type of soft tip.

As can be best seen in FIG. 6, the sound tube portion 44 is laterally offset with regard to the interface portion 40 in two dimensions, i.e. both with regard to the longitudinal and the transverse direction of the interface portion 40. By "laterally offset" it is meant that, when seen as a projection along the axial direction of the sound tube portion, the sound tube portion 44 is displaced with regard to any symmetry axis of the interface portion 40; in particular, the sound tube portion 44 is located "outside" the interface portion 40 in the view of FIG. 6. The arrangement of the sound tube portion 44 with regard to the interface portion 40 is eccentric and asymmetric.

The receptacle 42 has a substantially cup-like shape with a flat upper rim 50. It extends substantially perpendicular to the axial direction of the sound tube portion 44.

Figure 5:
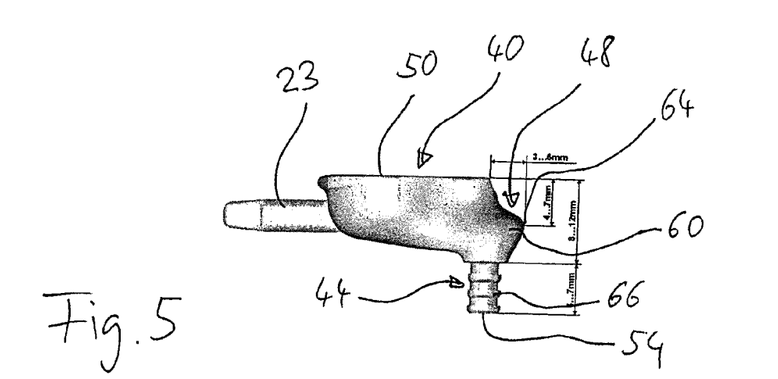
FIG. 5 is a side view of the earpiece of FIGS. 2 and 3.

As can be best seen in FIG. 6, the cross section of the receptacle 42 in a plane perpendicular to the sound tube portion 44 has a substantially pear-like shape, wherein the "elongate" end 52 of the receptacle 42 is adjacent to the engagement portion 48. The outer contour of the interface portion essentially corresponds to the shape of the receptacle and likewise has a pear-like shape. Preferably, the width of the interface portion 40 is from 8 to 14 mm, while the length of the interface portion 40 is from 13 to 20 mm. The interface portion 40 is "flat" in the sense that the dimension along the axial direction of the sound tube portion 44 is smaller than the dimension along a direction perpendicular thereto. As can be seen in FIG. 5, the dimension along the axial direction of the sound tube portion 44, i.e. the "height", preferably is about 8 to 12 mm.

The active unit 24 comprises two spring clips 56 for detachable engagement with corresponding mating structures 58 provided within the receptacle 42. In the example shown in FIGS. 4A, 4B and 7 the active unit comprises a boom microphone 16 carried by a bow 68.

The sound channel 26 extends from the elongate end 52 of the receptacle 42 through the engagement portion 48 and the sound tube portion 44 to a sound outlet opening 54 at the end of the sound tube portion 44.

The engagement portion 48 connects the interface portion 40 and the sound tube portion 44 and it has substantially a knee-like shape with a bead-like ridge portion 60 which projects in a direction perpendicular to the axial direction of the sound tube portion 44. The ridge portion extends like a helicoidal spiral starting from the upper end of the sound tube portion 44 and terminating in an end portion 62 which is oriented substantially tangential with regard to the interface portion 40. The end portion 62 of the ridge portion 60 is adapted to detachably connect with the retention element 23. The ridge portion 60 partly surrounds the sound channel and the elongate end 52 of the receptacle 42.

The "top", i.e., the rounded edge indicated at 64 in FIG. 5, of the ridge portion 60 preferably is located 4 to 7 mm below the upper end 50 of the interface portion 40 and at a distance of 3 to 6 mm from that end of the interface portion 40 which is closer to the sound tube portion 44.

Figure 9:
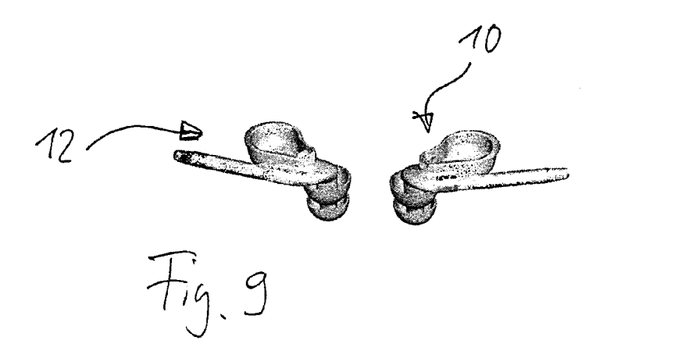
FIG. 9 is perspective view of a pair of earpieces for the right ear and the left ear, respectively.

As can be best seen in FIG. 9, the geometry of the earpiece 10 for the left ear and the earpiece 12 for the right ear is mirror symmetrical.

Retention of the earpiece within the concha is particularly promoted by the following features:

the engagement portion comprises a bead-like ridge portion which projects in a direction perpendicular to the sound tube portion;

the ridge portion extends like a helicoidal spiral starting from the sound tube portion and terminating in an end portion which is oriented substantially tangential with regard to the interface portion and substantially perpendicular with regard to the axial direction of the sound tube portion, wherein the end portion of the ridge portion is adapted to detachably connect with the retention element in such a manner that the retention element extends substantially perpendicular to the axial direction of the sound tube portion and substantially tangential with regard to the interface portion;

the sound tube portion is flexible with regard to bending forces;

the sound tube portion is laterally offset with regard to the interface portion;

the interface portion extends substantially perpendicular to the sound tube portion;

the cross section of the interface portion in a plane perpendicular to the sound tube portion has a substantially pear-like shape;

the specific dimensions of the earpiece:

the top of the ridge portion is located 4 to 7 mm below the upper end of the interface portion, the top of the ridge portion is located at a distance of 3 to 6 mm from that end of the interface portion which is closer to the sound tube portion, the width of the interface portion is from 8 to 14 mm, the length of the interface portion is from 13 to 20 mm, the sound tube portion has an axial length of 4 to 7 mm.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

The invention claimed is:

1. A hearing system, comprising:
   at least one earpiece to be worn at least partly in a user's ear canal, the at least one earpiece having a shell, an elongate retention element attached to the shell for retaining the shell within the user's ear canal, and an insert unit, the shell having a substantially straight sound tube portion carrying a soft tip which is to be inserted into the user's ear canal, an outwardly oriented interface portion for detachably receiving the insert unit, and an engagement portion located between the substantially straight sound tube portion and the interface portion for engaging with the tragus/anti-tragus region of the ear, wherein a material and dimensions of the retention element are such that the retention element is engageable with a user's concha by manual deformation by the user, and wherein the insert unit is one of a filter unit with at least one of a sound attenuation filter and an active electronic unit with at least a loudspeaker, and
   an external electronic unit, which is to be worn on a user's body below a user's neck, the external electronic unit being connected to the active electronic unit via a cable connection
   wherein the substantially straight sound tube portion is laterally offset relative to the interface portion in such a manner that, when seen as a projection along an axial direction of the substantially straight sound tube portion, the substantially straight sound tube portion is displaced from any symmetry axis of the interface portion, and
   wherein the engagement portion comprises a sound channel extending from the interface portion to the substantially straight sound tube portion, the sound channel of the engagement portion being angled relative to the axial direction of the substantially straight sound tube portion.

2. The system of claim 1, wherein the engagement portion is arranged to connect the interface portion and the sound tube portion.

3. The system of claim 2, wherein the sound channel of the engagement portion extends from the interface portion to the sound tube portion.

4. The system of claim 3, wherein the engagement portion is substantially knee-shaped.

5. The system of claim 3, wherein the engagement portion has a length of 8 to 12 mm with regard an axial direction of the sound tube portion.

6. The system of claim 1, wherein the engagement portion comprises a bead-shaped ridge portion which projects in a direction perpendicular to the sound tube portion.

7. The system of claim 6, wherein a top of the ridge portion is located 4 to 7 mm below an upper end of the interface portion.

8. The system of claim 6, wherein a top of the ridge portion is located at a distance of 3 to 6 mm from that end of the interface portion which is closer to the sound tube portion.

9. The system of claim 6, wherein the ridge portion has a helicoidal spiral shape that extends starting from the sound tube portion and terminating in an end portion which is oriented substantially tangential with regard to the interface portion and substantially perpendicular with regard to an axial direction of the sound tube portion.

10. The system of claim 9, wherein the ridge portion partly surrounds the sound channel.

11. The system of claim 10, wherein the ridge portion partly surrounds an elongate end of the interface portion.

12. The system of claim 11, wherein the interface portion extends substantially perpendicular to the sound tube portion.

13. The system of claim 12, wherein a cross section of the interface portion in a plane perpendicular to the sound tube portion is substantially pear-shaped.

14. The system of claim 13, wherein a width of the interface portion is from 8 to 14 mm.

15. The system of claim 14, wherein a length of the interface portion is from 13 to 20 mm.

16. The system of claim 9, wherein an end portion of the ridge portion is adapted to detachably connect with the retention element.

17. The system of claim 13, wherein the elongate end of the interface portion is adjacent to the engagement portion.

18. The system of claim 1, wherein the interface portion has a flat upper rim.

19. The system of claim 1, wherein the interface portion comprises a receptacle for receiving the active unit.

20. The system of claim 19, wherein the receptacle is substantially cup-shaped.

21. The system of claim 20, wherein the insert unit comprises a spring clip for detachable engagement within the receptacle.

22. The system of claim 21, wherein the sound tube portion is at least one of flexible with regard to bending forces and twistable.

23. The system of claim 1, wherein the soft tip is made of foam or of silicone.

24. The system of claim 1, wherein the soft tip is exchangeable.

25. The system of claim 1, wherein the sound tube portion has an axial length of 4 to 7 mm.

26. The system of claim 1, wherein the sound tube portion is laterally offset with regard to the interface portion.

27. The system of claim 26, wherein the sound tube portion is laterally offset with regard to the interface portion in two dimensions.

28. The system of claim 1, wherein the geometry of the earpiece for the left ear and the earpiece for the right ear is mirror symmetrical.

29. The system of claim 1, wherein the retention element is made of a material having a hardness of 60 Shore A to 90 Shore A.

30. The system of claim 1, wherein the retention element is fixed at the shell in a detachable manner for replacement of the retention element.

31. The system of claim 1, wherein the retention element is substantially straight.

32. The system of claim 31, wherein the retention element has a constant cross section with a tapered end.

33. The system of claim 1, wherein the retention element extends substantially perpendicular to an axial direction of the sound tube portion and substantially tangential with regard to the interface portion.

34. The system of claim 1, wherein the retention element is located below an upper end of the interface portion.

35. The system of claim 1, wherein the earpiece is adapted to provide for an acoustic attenuation of at least 10 dB averaged over an audible frequency range when worn by the user.

36. The system of claim 35, wherein the active unit comprises an ambient microphone for capturing ambient sound, and wherein the external unit comprises an audio signal processing unit for processing the audio signals captured by the ambient microphone in order to supply the processed audio signals to the loudspeaker of the active unit for realizing a sound level dependent active hearing protection function.

37. The system of claim 1, wherein the active unit comprises at least one microphone for capturing a user's voice.

38. The system of claim 37, wherein the microphone for capturing the user's voice is a boom microphone.

39. The system of claim 37, wherein the microphone for capturing the user's voice is an ear microphone oriented acoustically inwardly towards the user's ear canal.

40. The system of claim 39, wherein the active unit comprises an ambient microphone oriented acoustically outwardly towards an environment and wherein the external unit comprises an audio signal processing unit for processing audio signals from the ear microphone and the ambient microphone by a blind source separation algorithm adapted to separate the user's voice from ambient sound.

41. The system of claim 1, wherein the external unit comprises a wireless communication device for exchanging audio signals with another wireless communication device.

42. The system of claim 41, wherein the wireless communication device is a mobile phone or a radio device.

43. The system of claim 41, wherein the system is adapted to be powered by the wireless communication device.

* * * * *